United States Patent [19]

Schön et al.

[11] Patent Number: 4,755,520
[45] Date of Patent: Jul. 5, 1988

[54] SPARTEIN COMPOUNDS, THEIR PREPARATION AND USE

[75] Inventors: Uwe Schön, Burgdorf; Wolfgang Kehrbach, Hanover; Bernd Hachmeister, Isernhagen; Gerd Buschmann, Hanover; Ulrich G. Kühl, Gehrden, all of Fed. Rep. of Germany

[73] Assignee: Kali-Chemie Pharma GmbH, Hanover, Fed. Rep. of Germany

[21] Appl. No.: 875,311

[22] Filed: Jun. 17, 1986

[30] Foreign Application Priority Data

Jun. 22, 1985 [DE] Fed. Rep. of Germany ....... 3522475

[51] Int. Cl.$^4$ ................... A61K 31/435; C07D 471/22
[52] U.S. Cl. ....................................... 514/286; 546/63
[58] Field of Search ........................... 546/63; 514/286

[56] References Cited

U.S. PATENT DOCUMENTS 4,415,577 11/1983 Hachmeister et al. ............. 514/286

FOREIGN PATENT DOCUMENTS 25069 3/1981 European Pat. Off. ............ 514/286
2360475 6/1975 Fed. Rep. of Germany .

OTHER PUBLICATIONS

Rink et al., "17-Hydroxysparteine", Chemical Abstracts, vol. 51, No. 11, Col. 8114, Abstract No. 8114d.
Nowacki et al., "Conversion of Oxosparteines into Phenyl-...", Chemical Abstracts, vol. 67, No. 5, Abstract No. 22070h.

Burger, ed., *Medicinal Chemistry*, 2nd ed., Interscience Pub. (1960), p. 42.

*Primary Examiner*—Donald G. Daus
*Assistant Examiner*—William A. Teoli, Jr.
*Attorney, Agent, or Firm*—Foley & Lardner, Schwartz, Jeffery, Schwaab, Mack, Blumenthal & Evans

[57] ABSTRACT

Compounds of Formula (I)

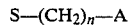

in which
S is a 17-spartein nucleus
n is 0 or 1
and A is 2-furyl, 2-thienyl or 2-(N-alkyl)pyrryl when n=0, or 3-furyl or 3-thienyl when n=1, or pyridyl or a phenyl group of Formula (II)

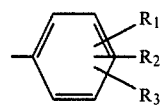

in which at least one of $R_1$, $R_2$ and $R_3$ is a defined substituent other than hydrogen. Such compounds and corresponding compounds in which A is an unsubstituted phenyl group are useful in pharmaceutical compositions as heart affecting agents. Methods of preparing such compounds and pharmaceutical compositions are also disclosed.

5 Claims, No Drawings

SPARTEIN COMPOUNDS, THEIR PREPARATION AND USE

BACKGROUND OF THE INVENTION

This invention relates to new aromatic compounds of the spartein series, to their use and to a method for their preparation. It also relates to medicaments which contain such compounds and to methods for the preparation of such medicaments.

Spartein, an alkaloid which can be extracted from broom (*Cytisus scoparius*), and its properties, which affect the heart and in particular influence the heart rhythm, have already been described in the technical literature.

An increase in effect with regard to extension of the refractory period can be achieved with sparteins substituted in position 17 by alkyl, i.e. compounds which have the following structure:

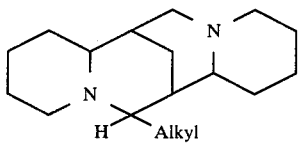

Such compounds are described in DE-OS No. 23 60 475. Also, a dimeric spartein with antiarrhythmic effect, 17,17'-bisspartein, is described in published European patent application No. EP 46,565 (U.S. Pat. No. 4,415,577).

The compounds of the prior art display good properties in the treatment of heart rhythm complaints, but their activity patterns could still be improved upon.

SUMMARY OF THE INVENTION

It is an object of the invention to provide new spartein derivatives with a modified activity pattern.

This and other objects of the invention are achieved by providing an aromatic compound corresponding to the Formula (I)

$$S-(CH_2)_n-A \qquad (I)$$

in which
S is a 17-spartein nucleus,
n is 0 or 1
and A is 2-furyl, 2-thienyl or 2-(N-alkyl)pyrryl when n=0, or 3-furyl or 3-thienyl when n=1, or pyridyl or substituted phenyl of Formula (II)

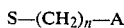

in which $R_1$, $R_2$ and $R_3$ are independently selected from the group consisting of hydrogen, alkyl, alkoxy, fluorine, chlorine, bromine, trifluoromethyl,

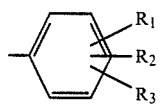

hydroxy, or —CO—$R_4$ in which $R_4$ is hydrogen, alkoxy, hydroxy, amino or substituted amino, or two adjacent ones of $R_1$, $R_2$ and $R_3$ together form an alkylene dioxy group; at least one of $R_1$, $R_2$ and $R_3$ being other than hydrogen; or a pharmacologically usable acid addition salt thereof.

In other aspects of the invention, the objects are achieved by providing methods of producing the aforedescribed compounds, pharmaceutical compositions comprising such compounds or corresponding compounds in which A represents an unsubstituted phenyl group and methods of preparing such pharmaceutical compositions.

DETAILED DESCRIPTION OF PREFERRED EMBODIMENTS

According to one aspect of the present invention there is provided an aromatic compound of the general Formula (I)

$$S-(CH_2)_n-A \qquad (I)$$

in which
S is a 17-spartein nucleus or group,
n is 0 or 1
and A is
(a1) 2-furyl, 2-thienyl or 2-(N-alkyl)-pyrryl when n=0, or
(a2) 3-furyl or 3-thienyl when n=1, or
(b) pyridyl or
(c) substituted phenyl or Formula (II)

in which, independently of each other, one or two of the groups $R_1$ to $R_3$ may be hydrogen and from at least one up to three of the groups $R_1$ to $R_3$ are independently selected from the group consisting of
(c1) alkyl
(c2) alkoxy
(c3) fluorine
(c4) chlorine
(c5) bromine
(c6) trifluoromethyl
(c7) two adjacent groups together forming alkylene dioxy

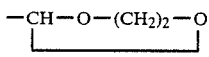

(c9) hydroxy
(c10) —CO—$R_4$
in which $R_4$ is hydrogen, alkoxy, hydroxy, amino or substituted amino; or a pharmacologically usable acid addition salt thereof.

Where A is a pyridyl group, this may be a 2-, 3- or 4-pyridyl group; preferably a 2- or 4-pyridyl group.

Where a substituent group is an alkyl group, this may be a straight chain or branched alkyl group and is preferably a lower alkyl group, that is to say an alkyl group with up to four carbon atoms. Preferred branched alkyl radicals, therefore, include isopropyl, sec.-butyl and (2-methylpropyl) groups, while the preferred straight chain groups are the methyl, ethyl, n-propyl and n-butyl groups.

Where a substituent group is an alkoxy group, it is preferably a lower alkoxy group, such as a methoxy, ethoxy, propoxy or butoxy group.

Where a substituent group is an alkylene dioxy group, it is preferably the group —O—(CH$_2$)$_q$—O— where q is 1 or 2.

According to one embodiment of the invention, none of the radicals $R_1$ to $R_3$ is a hydrogen atom. The corresponding compounds will be referred to hereinafter as "trisubstituted". An example of such a compound in the case where n=1 is the substitution 3,4,5-trimethoxy.

In another embodiment of the invention, one of the radicals $R_1$ to $R_3$ is a hydrogen atom. Such compounds are referred to as "disubstituted". Examples of such compounds in the case where n=1 are the substitutions 2,4-dimethyl, 2,3-dimethoxy, 2,4-dichloro, 2,6-dichloro, 3,5-dichloro, 2-fluoro-3-methyl, 2,6-difluoro, 2-fluoro-6-chloro and 3-methoxy-4-formyl.

A particular case of disubstitution is where two adjacent groups $R_1$ to $R_3$ together form an alkylene dioxy group. Examples of such compounds in the case where n=1 are the substituents 3,4-methylene dioxy and 3,4-ethylene dioxy.

In a further embodiment of the invention, two of the groups $R_1$ to $R_3$ are hydrogen atoms. Such compounds are referred to as "monosubstituted". The substituent in such a case may be in the ortho, meta or para position with respect to the connection with the spartein nucleus. If n=0 in Formula (I), monosubstituted compounds of the Formula (Vm)

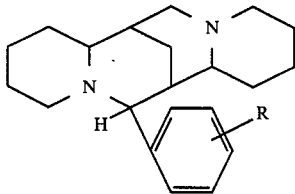

(Vm)

are preferred, in which R is a 3-methyl, 2-methoxy, 3-methoxy, 4-methoxy, 4-hydroxy, 2-trifluoromethyl, 3-trifluoromethyl, 4-trifluoromethyl, 3-fluoro, 4-fluoro, 3-chloro, 4-chloro, 4-bromo or 3-formyl group.

If n=1 in Formula (I), monosubstituted compounds of the Formula (VIm)

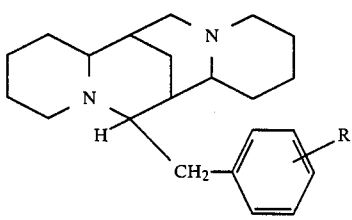

(VIm)

are preferred, in which R is a 2-methyl, 3-methyl, 4-methyl, 2-methoxy, 3-methoxy, 4-methoxy, 3-hydroxy, 2-fluoro, 3-fluoro, 4-fluoro, 2-chloro, 3-chloro, 4-chloro, 2-bromo, 3-bromo, 4-bromo, 3-trifluoromethyl, 4-formyl or 4-(N,N-diisopropyl)-aminocarbonyl group.

Those compounds of Formula (I) in which n is 1 are particularly preferred.

The invention also comprises medicaments, which contain at least one of the aforementioned compounds of Formula (I) or a pharmacologically usable addition salt thereof.

Suitable pharmacologically usable acid addition salts of the compounds of Formula (I) include water-soluble and water-insoluble salts of inorganic and organic acids, and specific examples of such salts include the hydrochloride, hydrobromide, hydroiodide, phosphate, nitrate, sulfate, perchlorate, acetate, citrate, gluconate, benzoate, propionate, butyrate, salicylate, sulphosalicylate, maleinate, laurate, fumarate, succinate, oxalate, tartrate, stearate, tosylate (p-toluene sulfonate), 2-hydroxy-3-naphthoate, 3-hydroxy-2-naphthoate, mesylate (methane sulfonate) and naphthalene sulfonate.

The invention further comprises medicaments, which contain as active ingredients at least one compound of the general Formula (I), in which A is an unsubstituted phenyl group, or a pharmacologically usable addition salt thereof. These unsubstituted phenyl compounds are already known (Rink, Grabowski, Archiv. d. Pharmazie, 289, 1956, page 702), but their pharmacological properties have never been described. Their use in therapeutic treatment is therefore new, and medicaments which contain these compounds are also new.

The invention also relates to a method for preparing medicaments which contain at least one compound of Formula (I), or a compound of Formula (I) in which A is an unsubstituted phenyl group, or a pharmacologically usable acid addition salt thereof. This method consists of mixing the appropriate compounds with one or more inert, pharmacologically suitable carrier substances or adjuvants and of converting them in a known manner into galenical preparations. Such preparations may be, for example, tablets, dragees, capsules, powders, granulates, aqueous or oily suspensions, emulsions, syrups or solutions for oral administration, suppositories for rectal administration, suspensions for injection under sterile conditions, or solutions for parenteral administration.

The invention also provides a method of preparing a compound of Formula (I).

In a variant (i), 17-hydroxyspartein or a 17-dehydrospartein salt, in particular the perchlorate, is reacted with a Grignard compound of Formula (III)

A—(CH$_2$)$_n$—MgHal  (III)

in which n is 0 or 1, A has the meaning given above under (a1), (a2), (b), (c1) to (c8), and Hal denotes halogen, in particular bromine or chlorine, to form the correspondingly substituted compound of Formula (I).

In a variant (ii), a 17-dehydrospartein salt, in particular the perchlorate, is reacted with an organometallic compound of Formula (IV)

A—(CH$_2$)$_n$—Li  (IV)

in which n is 0 or 1 and A has the meaning given above under (a1), (b), (c1) to (c8), to form the correspondingly substituted compound of Formula (I).

The preparation of the compounds of the Formulae (III) and (IV) is known and takes place by the reaction of a compound of Formula (VII)

A—(CH$_2$)$_n$—Hal  (VII)

with magnesium, lithium or with an alkyl lithium, preferably n-butyl-lithium. Hal represents halogen, in particular bromine or chlorine.

A compound of the Formula (IV) in which n=1 may also be produced from a compound of the Formula (VIII)

   (VIII)

by deprotonating the activated methyl group attached to the aromatic ring with a strong base such as an alkyl lithium, preferably n-butyl lithium, or a lithium amide, preferably lithium diisopropyl amide. Activated methyl groups are contained, for example, in compounds of Formula (VIII) in which A is 2-pyridyl, 4-pyridyl, 2-(4,4-dimethyl-$\Delta^2$-oxazolino)-phenyl or phenyl substituted in position 2 to 4 by —CO—$R_4$, in which $R_4$ is substituted amino.

A compound of the Formula (IV) in which n=0 may also be obtained through direct deprotonation of activated ring hydrogen atoms from a compound of Formula (IX)

   (IX)

by means of an alkyl lithium. Activated ring hydrogen atoms exist, for example, on the phenyl group in a position adjacent to an alkoxy-, preferably methoxy-group, or in an alpha position of a furyl- or N-alkylpyrryl system.

The compounds of Formula (I) prepared in such a way may be obtained as such or in the form of their pharmacologically usable acid addition salts. However, they may also be further reacted to form other compounds of Formula (I) in accordance with the following variants:

(iii) a compound, in which A is 2- or 4-bromophenyl or (c2), is metalated with an alkyl lithium and is further reacted in a known manner to form a compound of Formula (I) in which A is (c1), (c3) to (c5) or (c10);

(iv) a compound, in which A is (c2), is reacted in a known manner to split off the alkoxy group and form a compound of Formula (I) in which A is (c9), or (v) a compound, in which A is (c8), is subjected to acid hydrolysis, to form the corresponding aldehyde.

The compounds resulting from variants (iii) to (v) may also be obtained as such or in the form of their pharmacologically usable acid addition salts.

The organometallic reactions are carried out with the exclusion of moisture (using an absolute solvent) and atmospheric oxygen (under inert gas atmosphere, e.g. nitrogen or argon).

Suitable inert, organic solvents include ethers (e.g. diethylether, tetrahydrofuran, dioxane and dimethoxy ethane) or hydrocarbons (e.g. hexane, cyclohexane or benzene), preferred solvents being diethylether, tetrahydrofuran and hexane or mixtures thereof.

In variant (i), the Grignard reagent (III) is first produced from the corresponding halide (VII) and finely divided magnesium in accordance with the conditions of the Grignard reaction (e.g. K. Nutzel, "Method zur Herstellung und Umwandlung magnesiumorganischer Verbindugen" ("Methods for the production and conversion of magnesium-organic compounds") in: Houben-Weyl, "Methoden der organischen Chemie" ("Methods of organic chemistry"), Vol. 13/2a, page 53 ff).

If necessary a catalyst, such as iodine or 1,2-dibromoethane, may be used to produce the Grignard reagent. The reaction temperature usually lies between ambient temperature and the boiling point of the solvent or solvent mixture.

Depending upon the steric and electronic properties of the halide (VII), the duration of the reaction may be from 30 minutes to several hours.

Alternatively, according to variant (ii) an organolithium reaction may be carried out to produce the compound (I). The production of the lithium intermediate stage takes place according to standard methods (e.g. H. Gilman, "The Metalation Reaction with Organolithium Compounds", in: *Organic Reactions,* Vol. 8, page 258 ff, or H. R. Rodriquez, "Heteroatom-Facilitates Lithiations", in *Organic Reactions,* Vol. 26, page 1 ff.), using for example reactants, such as metallic lithium, an alkyl lithium, such as for example n-butyl lithium, or a lithium amide such as lithium diisopropyl amide.

It is known that Lewis bases containing nitrogen increase the reactivity of the lithium compounds. Therefore, in an appropriate case a nitrogen containing Lewis base, such as for example N,N,N',N'-tetramethylethylene diamine (TMEDA) or 1,4-diazabicyclo-[2,2,2]-octane (DABCO), may optionally be used as a catalyst.

The reaction may be carried out at a temperature of from −78° C. to +40° C., and, depending upon the steric and electronic properties of the halide (VII), the duration of the reaction may be from 30 minutes to several hours.

The phenyl lithium derivatives formed according to method variant (iii) by reaction of a bromide or alkoxy compound with an alkyl lithium, preferably n-butyl lithium, may be reacted in a known manner to form other new compounds of Formula (I) (e.g. N. S. Narasimhan, R. S. Mali, "Synthesis" 1983, page 957 ff). Examples of such reactions include reactions with N,N-dimethylformamide and alkyl halides.

The splitting off of the alkoxy radical according to variant (iv) takes place by known methods such as treatment with hydroiodic acid, boron tribromide, boron trichloride or phosphorus pentachloride, but preferably with hydroiodic acid.

The reactions may be carried out at normal (atmospheric) pressure, or at elevated pressure, but preferably at normal pressure, and the reaction temperatures may vary according to the method in a range from −78° C. to +200° C.

Any purification of the resulting compounds which may be necessary can be carried out in a conventional manner, e.g. through acid/base separation or by chromatographic methods.

The acid addition salts which are obtainable according to the invention are obtained in the known manner by a reaction of the basic compounds (I) with acids which form pharmacologically usable salts.

The compounds of Formula (I) and their pharmacologically usable acid addition salts are distinguished by interesting pharmacological properties and show in particular oxygen-conserving effects, frequency-influencing effects, and rhythmizing effects on the heart. The new compounds are distinguished by a good efficacy and high tolerability.

Thus, the new compounds show even at low doses a marked lowering of heart frequency and also an additional antiarrhythmic effect. Moreover, the undesired negative influence on the contractility of the heart is extremely low. This means that the compounds have a particularly favorable ratio of heart frequency lowering effect or extension of the refractory period of the heart to negatively inotropic side-effects, and consequently they have a large therapeutic range.

The influence of the active substance on the myocardial oxygen consumption was investigated in narcotised rats, and was calculated by the method of Neill (Neill, H. H. Levine, R. J. Wagman, R. Gorlin, "Circulation Research", 12 (1963), 163). The circulation measurements of systolic blood pressure and heart frequency which are necessary for this method were determined in the procedure according to Buschmann et al., (G. Buschmann, W. Schumacher, R. Budden and U. G. Kuhl, "J. Cardiovasc. Pharmacol. 2" (1980), 777 to 795). As can be seen from the following Table A, the active compounds reduce the double product of heart frequency and systolic blood pressure and thereby lead to a conservation of oxygen in the heart.

TABLE A

Influence on Heart Frequency (FRQ), Systolic Blood Pressure ($P_s$) and the Double Product (DP) in Narcotised Rats

| Substance | Dose [μmol/kg i.v.] | FRQ [1/min] | $P_s$ [mmHg] | DP [mmHg/min × 100] | Change DP [percentage] |
|---|---|---|---|---|---|
| Example 2 | -(Initial values) | 368 | 123 | 453 | — |
| No. 218* | 6.6 | 254 | 124 | 312 | − 29 |
| Example 2 | -(Initial values) | 408 | 124 | 506 | — |
| No. 221* | 2.6 | 306 | 121 | 376 | − 26 |

*used as dihydrochloride

Evidence of the antiarrhythmic effect of the new substances was obtained experimentally by determining the functional refractory period of the left auricle of the heart of female Albino Pirbright-white guinea pigs weighing 300 to 400 g by means of paired electrical stimulation following Govier's method (W. C. Govier, "J. Pharmacol. Exp. Ther.", 148 (1) (1965), 100 to 105). All the antiarrhythmic preparations of differing chemical structure currently used in therapy are distinguished by an extension of the functional refractory period. In addition, the method enables a determination of the effects of the test substance on the contractility of the heart muscle. In Table B, therefore, there is indicated as FRP 125% the concentration of μmol/l at which an extension of the functional refractory period to 125% occurs 18 minutes after administration of the test substance or respectively as F 75% the corresponding concentration which brings about a reduction in the contractility to 75% of the initial value.

The direct influence of the active substance on heart frequency (FRQ) was tested on spontaneously beating, isolated right auricles of female Albino Pirbright-white guinea pigs weighing 300 to 400 g. In Table B the concentration in μmol/l at which a decrease of frequency to 75% of the initial value occurs 20 minutes after the substance is administered is indicated as FRQ 75%.

The quotient F 75%/FRQ 75% of the contractility reducing dose and the heart frequency lowering dose is also indicated. This quotient gives information on the therapeutic range of the substances in relation to the heart frequency lowering effect.

It can be seen from Table B that the new substances do not display any appreciable undesired negatively inotropic effects; however, even at a very low concentration, they exhibit a heart frequency lowering and an antiarryhythmic effect.

TABLE B

Influence on the Frequency (FRQ) of Spontaneously Beating Right Guinea Pig Auricles and on the Contractility (F) and Functional Refractory Period (FRP) of Electrically Stimulated Left Guinea Pig Auricles

| Test Substance of Formula (I) | Effective Concentration (μmol/l) | | | Quotient F 75% / FRQ 75% |
|---|---|---|---|---|
| | FRQ 75% | F 75% | FRP 125% | |
| Ex. 2 No. 218* | 2.06 | >46.4 | 6.24 | >22.6 |
| Ex. 2 No. 221* | 0.99 | >46.4 | 2.17 | >46.8 |
| Pentyl spartein** | 7.5 | 22.1 | 9.1 | 2.9 |

* = used as dihydrochloride
** = used as salt with 2.3 moles L(+)-tartaric acid

Table B also gives the result using the compound known in literature as super-acidic pentyl spartein-L(+)-tartrate (EP-A-No. 00 25 069). The comparison clearly shows the surprising therapeutic range in relation to the heart frequency lowering effect of the compounds according to the invention compared with that of the known substance.

The superior activity of the substances according to the invention is therefore characterized by the combination of oxygen-conserving, rhythmizing and frequency-influencing effects on the heart. This activity pattern permits use in ischaemic heart disease, e.g. angina pectoris and myocardial infarction, and also in life-threatening arrhythmias.

The doses which are to be used vary, of course, according to the nature of the substance used, the manner of administration and the condition which is to be treated. In general, however, satisfactory results are obtained in animal experiments with doses of 0.01 to 100 mg/kg body weight.

The following Examples are intended to explain the preparation of the new compounds of Formula (I) in greater detail, but not to restrict the scope of the invention in any way.

The structures of the new compounds were established by spectroscopic investigations, in particular by analysis of the NMR-, mass-, IR- and/or UV-spectra.

The 17-hydroxyspartein was obtained from spartein in accordance with DE-OS No. 28 25 117.

The 17-dehydrospartein perchlorate was produced from 17-hydroxyspartein in accordance with M. Rink and K. Grabowski, "Arch. Pharm.", 289, (1965) 695.

The following abbreviations are used in the Examples and Tables:
SOL=solvent,
THF=tetrahydrofuran,
Et=diethyl ether,
T=temperature (°C.),
Cat=catalyst,
P=17-dehydrosparteinperchlorate,
H=17-hydroxyspartein,
DBE=1,2-dibromoethane, TS=tartaric acid salt,
HFu=fumaric acid salt.

EXAMPLE 1

Preparation of Compounds of Formula (III) or Formula (IV)

(1a) Preparation of compounds of Formula (III)

0.1 mole Magnesium chips are placed in 50 ml absolute solvent. If required, catalyst is added. After the dropwise addition of 0.1 mole of compound of Formula (VII) in 50 ml solvent, the formulation is kept at reflux until the magnesium is dissolved.

The reaction mixture is used as such for the reaction in Example 2.

(1b) Preparation of compounds of Formula (IV)

4.4 mmole n-butyl lithium (as a 15% solution in hexane) are dissolved in 30 ml absolute solvent at −78° C. After the slow dropwise addition of 4.5 mmole of compound of Formula (VII) in 30 ml solvent, stirring takes place for a further 30 minutes at −78° C. This reaction mixture is used for the reaction in Example 3.

(1c) Preparation of compounds of Formula (IV)

0.1 mole of a compound of formula (VIII) is added dropwise to a solution of 0.1 mole lithium-diisopropylamide—produced in situ from diisopropylamine and n-butyl lithium—in 100 ml absolute solvent at a corresponding temperature, and stirred. Thereafter, the mixture is diluted with 200 ml solvent, and the resulting reaction mixture is used for the reaction in Example 3.

(1d) Preparation of compounds of Formula (IV)

62.5 ml of a 1.6 molar solution of n-butyl lithium in hexane are added dropwise to 0.1 mole of a compound of Formula (IX) in 50 ml solvent, optionally in the presence of an approximately equimolar quantity of catalyst, under cooling (T1). In order to complete the deprotonation, the reaction mixture is stirred further at an elevated temperature (T2). The resulting reaction mixture is used for the reaction in Example 3, whereby the temperature is previously adjusted to T3.

Details regarding particular reaction conditions can be found in Tables (1a) to (1d).

EXAMPLE 2

Preparation of a compound of Formula (I) according to Variant (i)

0.05 mole 17-hydroxyspartein or 17-dehydrosparteinperchlorate in 100 ml solvent are added to the reaction mixture derived from Example (1a) and heated under reflux up to complete reaction. After careful acidification with dilute hydrochloric acid and subsequent acid/base separation and chromatography on neutral aluminum oxide or silica gel with an ether/hexane mixture as a mobile solvent, the compound of Formula (I) is isolated. If desired, this compound may be converted into its acid addition salt. Particular reaction conditions and products are shown in Table 2.

EXAMPLE 3

Preparation of a compound of Formula (I) according to Variant (ii)

An equimolar quantity of solid 17-dehydrosparteinperchlorate is added to the reaction mixture obtained from Example (1b) or (1c) or (1d) and is further stirred with slow heating to ambient temperature to complete the reaction.

After addition of dilute acid or ice-water, the reaction mixture is worked up as in Example 2. Details regarding particular reaction conditions and products obtained are given in Table 3.

EXAMPLE 4

Preparation of a compound of Formula (I) according to Variant (iii)

0.013 mole educt are dissolved in absolute solvent with catalyst being added if required. Under cooling, 0.02 mole n-butyl lithium (as a 15% solution in hexane) are added dropwise and, after stirring at ambient temperature for 1 to 6 hours, 0.04 mole N,N-dimethylformamide in 20 ml solvent are added. After completion of the reaction, water is added, and the reaction mixture is worked up as in Example 2. Particular reaction conditions and products obtained are characterized in Table 4.

EXAMPLE 5

Preparation of a compound of Formula (I) according to Variant (iv)

30 ml 57% hydroiodic acid are added slowly dropwise to 0.017 mole educt in 14 ml acetic anhydride. The formulation is heated under reflux for 4 hours. The reaction mixture is carefully introduced into ice-water and is worked up as indicated under Example 2. Details regarding reaction conditions and products obtained are shown in Table 5.

EXAMPLE 6

Preparation of a compound of Formula (I) according to Variant (v)

0.02 mole magnesium are placed in 50 ml absolute THF. After activation with 0.2 ml 1,2-dibromoethane, 0.02 mole 2-(3-bromophenyl)-1,3-dioxolane in 10 ml absolute THF are added dropwise. After the formulation has been heated for 1 hour at reflux, it is diluted with 100 ml absolute THF and mixed with 0.01 mole 17-dehydrospartein perchlorate, and reheated to complete the reaction.

In order to form the free aldehyde, the reaction solution is mixed with dilute hydrochloric acid and stirred for 30 minutes at ambient temperature. After acid/base separation and subsequent filtration over alumina with ether/hexane (1:1) as mobile solvent, the formyl derivative can be isolated as an oil. By reaction with three equivalents tartaric acid, a crystalline tartrate is obtained (melting point: 126° to 130° C.).

The following Examples 7 through 9 describe pharmaceutical preparations containing the active substances according to the invention and also the production of such pharmaceutical preparations.

EXAMPLE 7

Tablets

| Composition: | |
|---|---|
| Active substance (Example 2, No. 218) | 20 parts |
| Corn Starch | 30 parts |
| Lactose | 55 parts |
| Polyvinyl pyrrolidone | 5 parts |
| Magnesium stearate | 2 parts |
| Hydrogenated castor oil | 1 part |
| Total | 113 parts |

Directions for preparation:

The active substance is mixed with the corn starch and lactose powder in a mixer. The resulting mixture is thoroughly moistened with a 20% solution of polyvinyl pyrrolidone (Kollidon 25 TM from BASF) in isopropanol. If required, further isopropanol is added. The moist granulate is passed through a 2 mm screen, dried at 40° C. on latticed screens and is then passed through a 1 mm screen (Frewitt machine). After mixing the granulate with magnesium stearate and hydrogenated castor oil, tablets of 113 mg are formed by pressing so that each tablet contains 20 mg of active substance.

EXAMPLE 8

Capsules

| Composition | |
|---|---|
| Active substance (Example 2, No. 218) | 20 parts |
| Corn starch | 20 parts |
| Lactose | 45 parts |
| Polyvinyl pyrrolidone | 3 parts |
| Magnesium stearate | 1.5 parts |
| Silica aerogel | 0.5 parts |
| Total | 90 parts |

Directions for preparation:

The active substance is mixed with corn starch and lactose powder in a mixer. The resulting mixture is thoroughly moistened with a 20% solution of polyvinyl pyrrolidone (Kollidon 25 TM from BASF) in isopropanol. If required, further isopropanol is added. The moist granulate is passed through a 1.6 mm screen (Frewitt), dried at 40° C. on latticed screens and is then passed through a 1 mm screen (Frewitt). After the mixing of the granulate with magnesium stearate and silica aerogel (Aerosil 200 TM from DEGUSSA), 90 mg portions thereof are filled by means of an automatic capsule machine into size 4 hard gelatine capsules so that each capsule contains 20 mg active substance.

EXAMPLE 9

Ampoules

| Composition (per ampoule): | |
|---|---|
| Active substance (Example 2, No. 218) | 5 mg |
| Sodium chloride | 16 mg |
| Water for injection purposes ad | 2.0 ml |

Directions for preparation:

The sodium chloride is dissolved in water for injection purposes, the active substance is added and dissolved under stirring. Filling takes place up to the final volume with sufficient water for injection purposes. The formulation is passed through a 0.25μ membrane filter. Brown glass ampoules are each filled with 2.15 ml and are sealed by melting. Sterilization with steam is carried out at 121° C. for 30 minutes. 2 ml injection solution contain 5 mg active substance.

TABLE 1a

Preparation of compounds of Formula (III) from compounds of Formula (VII)

| Example | SOL | Cat | A | n | Hal |
|---|---|---|---|---|---|
| 100 | THF | — | 2-thienyl | 0 | Br |
| 101 | Et | iodine | phenyl | 0 | Br |
| 102 | Et | iodine | 2-methoxy-phenyl | 0 | Br |
| 103 | Et | iodine | 3-methoxy-phenyl | 0 | Br |
| 104 | Et | iodine | 4-methoxy-phenyl | 0 | Br |
| 105 | Et | iodine | 3,4-methylene dioxyphenyl | 0 | Br |
| 106 | Et | iodine | 3,4-ethylene dioxyphenyl | 0 | Br |
| 107 | Et | iodine | 2-trifluoromethylphenyl | 0 | Br |
| 108 | Et | iodine | 3-trifluoromethylphenyl | 0 | Br |
| 109 | Et | iodine | 4-trifluoromethylphenyl | 0 | Br |
| 110 | Et | iodine | 3-chlorophenyl | 0 | Br |
| 111 | Et | iodine | 4-chlorophenyl | 0 | Br |
| 112 | Et | iodine | 3-fluorophenyl | 0 | Br |
| 113 | Et | iodine | 4-fluorophenyl | 0 | Br |
| 114 | THF | CH$_3$I | 3,4-dimethoxyphenyl | 0 | Br |
| 115 | THF | OCl$_4$ | 3-methylphenyl | 0 | Br |
| 116 | THF | | phenyl | 1 | Cl |
| 117 | Et | iodine | 2-methoxyphenyl | 1 | Cl |
| 118 | Et | iodine | 3-methoxyphenyl | 1 | Cl |
| 119 | Et | iodine | 4-methoxyphenyl | 1 | Cl |
| 120 | THF | DBE | 3,4,5-trimethoxyphenyl | 1 | Cl |
| 121 | Et | iodine | 2-chlorophenyl | 1 | Cl |
| 122 | Et | iodine | 3-chlorophenyl | 1 | Cl |
| 123 | Et | — | 4-chlorophenyl | 1 | Br |
| 124 | Et | — | 3-trifluoromethylphenyl | 1 | Cl |
| 125 | Et | — | 2-fluorophenyl | 1 | Br |
| 126 | Et | — | 3-fluorophenyl | 1 | Br |
| 127 | Et | — | 4-fluorophenyl | 1 | Br |
| 128 | Et | — | 2-bromophenyl | 1 | Br |
| 129 | Et | DBE | 3-bromophenyl | 1 | Br |
| 130 | Et | DBE | 4-bromophenyl | 1 | Br |
| 131 | Et | — | 3,4-dichlorophenyl | 1 | Br |
| 132 | Et | — | 2,6-dichlorophenyl | 1 | Br |
| 133 | Et | — | 2-methylphenyl | 1 | Br |
| 134 | Et | — | 3-methylphenyl | 1 | Br |
| 135 | Et | — | 4-methylphenyl | 1 | Br |
| 136 | Et | — | 2,4-dimethylphenyl | 1 | Cl |
| 137 | Et | — | 3,5-dichlorophenyl | 1 | Cl |
| 138 | Et | — | 2,6-difluorophenyl | 1 | Br |
| 139 | Et | — | 2-fluoro-3-methylphenyl | 1 | Br |
| 140 | Et | — | 2-chloro-6-fluorophenyl | 1 | Cl |

TABLE 1b

Preparation of compounds of Formula (IV) from compounds of Formula (VII)

| Example | SOL | A | n | Hal |
|---|---|---|---|---|
| 150 | THF | 2-pyridyl | 0 | Br |
| 151 | Et | 4-bromophenyl | 0 | Br |

TABLE 1c

Preparation of compounds of Formula (IV) from compounds of Formula (VIII)

| Example | SOL | T | A | n |
|---|---|---|---|---|
| 170 | THF | −78 | 4-pyridyl | 1 |
| 171* | THF | −78 | 2-pyridyl | 1 |
| 172** | THF | 0 | 2,3-dimethoxyphenyl | 1 |
| 173 | THF | 0 | 4-N,N—diisopropylbenzamide | 1 |
| 174* | Et | 0 | 2-(4,4-dimethyl-Δ$^2$-oxazolino)-phenyl | 1 |

Note:
*n-butyl lithium in place of diisopropylamide
**with the addition of TMEDA TABLE 1d Preparation of compounds of Formula (IV) from compounds of Formula (IX)

| Example | SOL | Cat | T$_1$ °C. | T$_2$ °C. | T$_3$ °C. | A | n |
|---|---|---|---|---|---|---|---|
| 190 | THF | — | −25 | −15 | 0 | 2-furyl | 0 |
| 191 | THF | TMEDA | 0 | +40 | −30 | 2-(N—methyl)pyrryl | 0 |

TABLE 2

Preparation of compounds of Formula (I) according to Variant i)

| Example | Spartein derivative | SOL | A | n | isolated form | MP °C. |
|---|---|---|---|---|---|---|
| 200 | P | THF | 2-thienyl | 0 | base | 84 |
| 201 | H | Et | phenyl | 0 | base | 105-107 |
| 202 | P | Et | 2-methoxyphenyl | 0 | 2 HCl | 220 |
| 203 | P | Et | 3-methoxyphenyl | 0 | 2 HCl | 208 |
| 204 | P | Et | 4-methoxyphenyl | 0 | 2 HCl | 238 |
| 205 | P | Et | 3,4-methylene dioxyphenyl | 0 | 2,33 TS | 145 |
| 206 | P | Et | 3,4-ethylenedioxyphenyl | 0 | 1,9 HFu | 187 |
| 207 | P | Et | 2-trifluoromethylphenyl | 0 | base | 130 |
| 208 | H | Et | 3-trifluoromethylphenyl | 0 | 2 HCl | amorphous |
| 209 | H | Et | 4-trifluoromethylphenyl | 0 | 2 HCl | amorphous |
| 210 | H | Et | 3-chlorophenyl | 0 | 3 TS | amorphous |
| 211 | H | Et | 4-chlorophenyl | 0 | 3,4 TS | amorphous |
| 212 | H | Et | 3-fluorophenyl | 0 | 3 TS | amorphous |
| 213 | H | Et | 4-fluorophenyl | 0 | 3,6 TS | amorphous |
| 214 | P | THF | 3,4-dimethoxyphenyl | 0 | base | 117 |
| 215 | P | THF | 3-methylphenyl | 0 | 2,3 HFu | amorphous |
| 216 | P | THF | phenyl | 1 | base | 68-71 |
| 217 | P | Et | 2-methoxyphenyl | 1 | base | 59 |
| 218 | P | Et | 3-methoxyphenyl | 1 | base | 51-52 |
| 219 | H | Et | 4-methoxyphenyl | 1 | base | 100 |
| 220 | P | THF | 3,4,5-trimethoxyphenyl | 1 | 2,8 TS | 103 |
| 221 | H | Et | 2-chlorophenyl | 1 | base | 115 |
| 222 | H | Et | 3-chlorophenyl | 1 | base | 76 |
| 223 | P | Et | 4-chlorophenyl | 1 | base | 120 |
| 224 | H | Et | 3-trifluoromethylphenyl | 1 | 2,8 HFu | amorphous |
| 225 | P | THF | 2-fluorophenyl | 1 | 2,25 TS | 126 |
| 226 | P | THF | 3-fluorophenyl | 1 | 2,15 TS | 138 |
| 227 | P | THF | 4-fluorophenyl | 1 | base | 74 |
| 228 | P | THF | 2-bromophenyl | 1 | base | 131 |
| 229 | P | THF | 3-bromophenyl | 1 | 2 TS | 138-140 |
| 230 | P | THF | 4-bromophenyl | 1 | base | 142 |
| 231 | P | THF | 3,4-dichlorophenyl | 1 | base | 80 |
| 232 | P | THF | 2,6-dichlorophenyl | 1 | 2,1 TS | 143 |
| 233 | P | THF | 2-methylphenyl | 1 | 2,1 TS | 140 |
| 234 | P | THF | 3-methylphenyl | 1 | base | 57 |
| 235 | P | THF | 4-methylphenyl | 1 | base | 58 |
| 236 | P | THF | 2,4-dimethylphenyl | 1 | base | 158-161 |
| 237 | P | THF | 3,5-dichlorophenyl | 1 | 2,1 TS | 130 |
| 238 | P | THF | 2,6-difluorophenyl | 1 | 2,2 TS | 135 |
| 239 | P | THF | 2-fluoro-3-methylphenyl | 1 | 2,1 TS | 139 |
| 240 | P | THF | 2-chloro-6-fluorophenyl | 1 | 2,2 TS | 131 |

TABLE 3

Preparation of compounds of Formula (I) according to Variant ii)

| Example | Formulation | n | A | isolated form | MP °C. |
|---|---|---|---|---|---|
| 350 | 1b | 0 | 2-pyridyl | 2 TS | 135 |
| 351 | 1b | 0 | 4-bromophenyl | 2,3 TS | 150 |
| 370 | 1c | 1 | 4-pyridyl | 3 TS | 120 |
| 371 | 1c | 1 | 2-pyridyl | base | 128 |
| 372 | 1c | 1 | 2,3-dimethoxyphenyl | 2 HCl | amorphous |
| 373 | 1c | 1 | 4-N,N—diisopropylamino-carbonylphenyl | 2,5 TS | 145-148 |
| 374 | 1c | 1 | 2-(4,4-dimethyl-$\Delta^2$-oxazolino)-phenyl | base | 112-119 |
| 390 | 1d | 0 | 2-furyl | 2,5 TS | 113 |
| 391 | 1d | 0 | 2-(N—methyl)-pyrryl | base | 118 |

TABLE 4

Preparation of compounds of Formula (I) according to Variant iii)

| Example | Educt | SOL | Cat | T | A | n | isolated form | MP °C. |
|---|---|---|---|---|---|---|---|---|
| 400 | 218 | THF | TMEDA | 0 | 3-methoxy-4-formyl-phenyl | 1 | 2,3 TS | 117-120 |
| 401 | 351 | THF | — | −30 | 4-formyl-phenyl | 0 | base | 106 |

TABLE 5

Preparation of compounds of Formula (I) according to Variant iv)

| Example | Educt | A | n | isolated form | MP °C. |
|---|---|---|---|---|---|
| 500 | 204 | 4-hydroxyphenyl | 0 | 2 HCl | amorphous |
| 501 | 218 | 3-hydroxyphenyl | 1 | base | 74-76 |

We claim:
1. A compound corresponding to the Formula (I)

$$S-(CH_2)_n-A \qquad (I)$$

wherein
S is a 17-spartein nucleus
n is 1, and
A is methoxyphenyl or chlorophenyl;
or a pharmacologically usable acid addition salt thereof.

2. A compound according to claim 1, wherein A is 3-methoxyphenyl or 2-chlorophenyl.

3. A compound according to claim 2, wherein A is 3-methoxyphenyl.

4. A pharmaceutical composition comprising a pharmaceutically suitable carrier or adjuvant and a compound corresponding to Formula (I)

$$S-(CH_2)n-A \qquad (I)$$

wherein
S is a 17-spartein nucleus,
n=1 and
A is methoxyphenyl or chlorophenyl;
or a pharmacologically usable acid addition salt thereof.

5. A pharmaceutical composition according to claim 4, wherein A is 3-methoxyphenyl.

* * * * *